US009903848B2

(12) United States Patent
Wong et al.

(10) Patent No.: US 9,903,848 B2
(45) Date of Patent: Feb. 27, 2018

(54) NON-DESTRUCTIVE INSPECTION METHOD WITH OBJECTIVE EVALUATION

(75) Inventors: John T. Wong, Bridgeport, CT (US); Dan Ursenbach, Hamden, CT (US)

(73) Assignee: Sikorsky Aircraft Corporation, Stratford, CT (US)

( * ) Notice: Subject to any disclaimer, the term of this patent is extended or adjusted under 35 U.S.C. 154(b) by 1584 days.

(21) Appl. No.: 13/142,608

(22) PCT Filed: Dec. 30, 2008

(86) PCT No.: PCT/US2008/088509
§ 371 (c)(1),
(2), (4) Date: Jun. 29, 2011

(87) PCT Pub. No.: WO2010/077240
PCT Pub. Date: Jul. 8, 2010

(65) Prior Publication Data
US 2011/0270537 A1    Nov. 3, 2011

(51) Int. Cl.
*G01N 33/20*  (2006.01)
*G01N 29/265* (2006.01)
*G01N 29/44*  (2006.01)

(52) U.S. Cl.
CPC .......... *G01N 33/20* (2013.01); *G01N 29/265* (2013.01); *G01N 29/4427* (2013.01); *G01N 29/4445* (2013.01); *G01N 2291/0231* (2013.01); *G01N 2291/0234* (2013.01); *G01N 2291/2694* (2013.01)

(58) Field of Classification Search
CPC ............. G01N 29/265; G01N 29/4427; G01N 29/4445; G01N 33/20; G01N 2291/0231; G01N 2291/0234; G01N 2291/2694

USPC ............................................................ 702/29
See application file for complete search history.

(56) References Cited

U.S. PATENT DOCUMENTS

| 3,575,043 | A |   | 4/1971  | Allen |
|-----------|---|---|---------|-------|
| 4,487,072 | A | * | 12/1984 | Livingston ..................... 73/622 |
| 4,636,644 | A |   | 1/1987  | Stokes |
| 4,896,278 | A |   | 1/1990  | Grove |
| 5,091,029 | A |   | 2/1992  | Davis et al. |
| 5,138,642 | A |   | 8/1992  | McCroskey et al. |
| 5,182,775 | A |   | 1/1993  | Matsui et al. |
| 5,198,679 | A |   | 3/1993  | Katoh |
| 5,379,336 | A |   | 1/1995  | Kramer et al. |
| 5,420,427 | A |   | 5/1995  | Morgan et al. |
| 5,570,207 | A |   | 10/1996 | Chang |

(Continued)

FOREIGN PATENT DOCUMENTS

WO    0206814    1/2002

OTHER PUBLICATIONS

Supplementary European Search Report for Application No. 08879313.8 dated Sep. 19, 2016.

(Continued)

*Primary Examiner* — Daniel Kessie
(74) *Attorney, Agent, or Firm* — Carlson, Gaskey & Olds, P.C.

(57) ABSTRACT

A method of non-destructive inspection evaluation includes converting a scan file of a part into a text file, determining whether the signal attenuation representative value is greater than a predetermined value and outputting a numeric score related to the signal attenuation representative value to signify a defect.

21 Claims, 9 Drawing Sheets

(56) References Cited

U.S. PATENT DOCUMENTS

| | | | |
|---|---|---|---|
| 5,591,913 A | 1/1997 | Tucker | |
| 5,614,720 A | 3/1997 | Morgan et al. | |
| 5,618,994 A | 4/1997 | Falsetti | |
| 5,821,541 A | 10/1998 | Tumer | |
| 5,824,908 A * | 10/1998 | Schindel et al. | 73/632 |
| 5,942,690 A | 8/1999 | Shvetsky | |
| 5,974,166 A | 10/1999 | Ino et al. | |
| 6,082,198 A | 7/2000 | Sabourin et al. | |
| 6,121,620 A | 9/2000 | Tashiro et al. | |
| 6,201,891 B1 | 3/2001 | Ino et al. | |
| 6,220,099 B1 | 4/2001 | Marti et al. | |
| 6,243,440 B1 | 6/2001 | Oikawa et al. | |
| 6,384,393 B2 | 5/2002 | Takami et al. | |
| 6,444,895 B1 | 9/2002 | Nikawa | |
| 6,463,169 B1 | 10/2002 | Ino et al. | |
| 6,479,827 B1 | 11/2002 | Hamamoto et al. | |
| 6,502,984 B2 | 1/2003 | Ogura et al. | |
| 6,516,098 B2 | 2/2003 | Nonaka | |
| 6,559,452 B1 | 5/2003 | Tashiro | |
| 6,600,160 B2 | 7/2003 | Kobayashi et al. | |
| 6,610,918 B2 | 8/2003 | Nikawa | |
| 6,641,535 B2 | 11/2003 | Buschke et al. | |
| 6,643,411 B2 | 11/2003 | Nonaka | |
| 6,720,775 B2 | 4/2004 | Plotnikov et al. | |
| 6,720,812 B2 | 4/2004 | Tumer et al. | |
| 6,731,718 B2 | 5/2004 | Ogura et al. | |
| 6,745,628 B2 * | 6/2004 | Wunderer | 73/579 |
| 6,751,342 B2 | 6/2004 | Shepard | |
| 6,759,259 B2 | 7/2004 | Nikawa | |
| 6,765,187 B2 | 7/2004 | Ishii et al. | |
| 6,789,427 B2 | 9/2004 | Batzinger et al. | |
| 6,798,453 B1 | 9/2004 | Kaifu | |
| 6,809,516 B1 | 10/2004 | Li et al. | |
| 6,818,899 B2 | 11/2004 | Endo | |
| 6,825,473 B2 | 11/2004 | Watanabe | |
| 6,872,949 B2 | 3/2005 | Mizuoka et al. | |
| 6,881,945 B2 | 4/2005 | Ishii et al. | |
| 6,890,302 B2 | 5/2005 | Oravecz et al. | |
| 6,934,360 B2 | 8/2005 | De Groot | |
| 6,934,409 B2 | 8/2005 | Ohara | |
| 6,950,545 B1 | 9/2005 | Nomoto et al. | |
| 6,952,015 B2 | 10/2005 | Kameshima | |
| 6,965,111 B2 | 11/2005 | Endo | |
| 6,967,332 B2 | 11/2005 | Kobayashi et al. | |
| 6,984,813 B2 | 1/2006 | Ishii et al. | |
| 7,002,157 B2 | 2/2006 | Kameshima | |
| 7,010,982 B2 | 3/2006 | Bergman | |
| 7,015,478 B2 | 3/2006 | Yamamoto | |
| 7,026,608 B2 | 4/2006 | Hirai | |
| 7,038,215 B2 | 5/2006 | Endo | |
| 7,042,980 B2 | 5/2006 | Endo | |
| 7,049,589 B2 | 5/2006 | Yamaguchi et al. | |
| 7,050,535 B2 | 5/2006 | Georgeson et al. | |
| 7,060,971 B2 | 6/2006 | Zombo et al. | |
| 7,077,120 B2 | 7/2006 | Funakoshi et al. | |
| 7,078,701 B2 | 7/2006 | Ishii et al. | |
| 7,081,629 B2 | 7/2006 | Endo | |
| 7,082,186 B2 | 7/2006 | Zhao et al. | |
| 7,082,187 B2 | 7/2006 | De Groot | |
| 7,098,461 B2 | 8/2006 | Endo | |
| 7,109,492 B2 | 9/2006 | Endo | |
| 7,119,339 B2 | 10/2006 | Ferguson et al. | |
| 7,126,129 B2 | 10/2006 | Yamamoto | |
| 7,126,386 B2 | 10/2006 | Tumer et al. | |
| 7,138,639 B2 | 11/2006 | Kameshima | |
| 7,148,487 B2 | 12/2006 | Ishii et al. | |
| 7,155,048 B2 | 12/2006 | Ohara | |
| 7,164,112 B2 | 1/2007 | Takami et al. | |
| 7,215,807 B2 | 5/2007 | Nomoto et al. | |
| 7,227,151 B2 | 6/2007 | Endo | |
| 7,233,867 B2 | 6/2007 | Pisupati et al. | |
| 7,235,789 B2 | 6/2007 | Kobayashi et al. | |
| 7,271,392 B2 | 9/2007 | Ishii et al. | |
| 7,302,039 B2 | 11/2007 | Takenaka et al. | |
| 7,315,609 B2 | 1/2008 | Safai et al. | |
| 7,345,767 B2 | 3/2008 | Amaya et al. | |
| 8,490,362 B2 * | 7/2013 | Kulesha | 52/636 |
| 2005/0167596 A1 | 8/2005 | Rothenfusser et al. | |
| 2005/0241397 A1 | 11/2005 | Bergman | |
| 2006/0008309 A1* | 1/2006 | Patton et al. | 400/120.1 |
| 2006/0283250 A1 | 12/2006 | Fair et al. | |
| 2006/0287836 A1 | 12/2006 | Mateo | |
| 2007/0045544 A1 | 3/2007 | Favro | |
| 2007/0047831 A1 | 3/2007 | Wen | |
| 2007/0175912 A1* | 8/2007 | Uehara et al. | 221/30 |

OTHER PUBLICATIONS

Prakash R et al, Ultrasonic Determination of Lay-up Order in Cross-plied CFRP, Composites, vol. 8, No. 2, Apr. 1, 1977, pp. 100-102.

Hsu D K et al, Ultrasonic Mapping the Ply Layup of Composite Laminates, Materials Evaluation, American Society for Nondestructive Testing, vol. 60, No. 9, Sep. 1, 2002, pp. 1099-1106, United States.

* cited by examiner

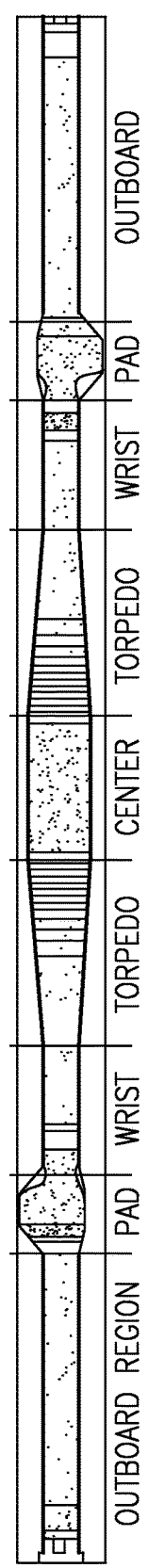
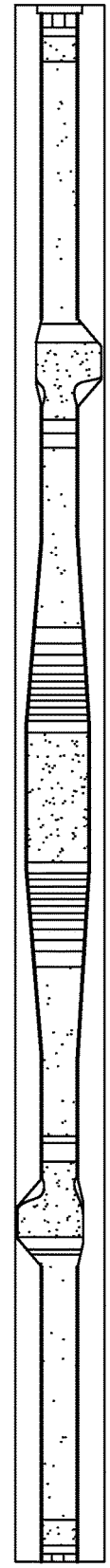
FIG.3
FIG.4A

| | A | B | C | D | E | F | G | H | I | J | K |
|---|---|---|---|---|---|---|---|---|---|---|---|
| 1 | | | Pad A | | | Pad B | | | | | |
| 2 | Serial No's | Mean | Std. Dev | Pixels | Mean | Std. Dev | Pixels | Pass/fail | | | |
| 3 | 13758 | 49.28448 | 3.175466 | 116 | 50.55357 | 3.484614 | 56 | <--Good! | | | |
| 4 | 13759 | 48.91379 | 4.433859 | 58 | 53.94118 | 0.242536 | 17 | <--Good! | | | |
| 5 | 13760 | 50.29444 | 4.357553 | 360 | 49.66151 | 3.647157 | 582 | <--Good! | | | |
| 6 | 13761 | 50.56892 | 2.734414 | 399 | 45.89076 | 5.712096 | 476 | <--Good! | | Run FiberwashScan | |
| 7 | 13762 | 52.37838 | 1.348764 | 111 | 49.24324 | 3.906554 | 185 | <--Good! | | | |
| 8 | 13763 | 49.67822 | 2.169536 | 202 | 50.47619 | 2.287166 | 42 | <--Good! | | | |
| 9 | 13764 | 50 | 0 | 0 | 47.2193 | 3.388577 | 114 | <--Good! | | | |
| 10 | 13765 | 51.85366 | 1.55822 | 41 | 47.07623 | 3.280919 | 223 | <--Good! | | | |
| 11 | 13766 | 50.49505 | 3.53447 | 101 | 49 | 3.809425 | 513 | <--Good! | | | |
| 12 | 13767 | 49.49096 | 5.401189 | 387 | 46.0884 | 5.215991 | 724 | <--Good! | | | |
| 13 | 13768 | 45.52119 | 5.907404 | 236 | 48.26455 | 4.371555 | 189 | <--Good! | | | |
| 14 | 13769 | 52.85 | 1.565248 | 20 | 47.43883 | 5.450527 | 376 | <--Good! | | | |
| 15 | 13770 | 48.70763 | 3.130377 | 236 | 51.90426 | 2.644 | 94 | <--Good! | | | |
| 16 | 13771 | 52.57616 | 1.00291 | 151 | 49.09081 | 3.771017 | 377 | <--Good! | | | |
| 17 | 13772 | 48.90164 | 2.711625 | 183 | 50.34969 | 2.765604 | 163 | <--Good! | | | |
| 18 | 13773 | 48.56647 | 5.197818 | 346 | 49.71912 | 4.508009 | 502 | <--Good! | | | |
| 19 | 13774 | 48.20183 | 7.032701 | 109 | 50 | 2.119675 | 216 | <--Good! | | | |
| 20 | 13775 | 52.86458 | 1.244946 | 96 | 53.12308 | 1.663089 | 65 | <--Good! | | | |
| 21 | 13776 | 51.97321 | 1.833974 | 336 | 48.81728 | 4.329338 | 301 | <--Good! | | | |
| 22 | 13777 | 46.05085 | 5.349091 | 118 | 43.33333 | 5.954877 | 132 | <--Good! | | | |
| 23 | 13778 | 51 | 3.095696 | 25 | 49.98876 | 3.084029 | 89 | <--Good! | | | |
| 24 | 13779 | 45.14836 | 7.377047 | 701 | 46.47117 | 6.802547 | 1110 | <--Fail | | | |
| 25 | 13780 | 51.71429 | 2.968886 | 21 | 49.34848 | 2.606465 | 132 | <--Good! | | | |
| 26 | 13781 | 52.97674 | 1.595953 | 43 | 50.44706 | 3.15293 | 170 | <--Good! | | | |
| 27 | 13782 | 51 | 3.165075 | 114 | 51.29508 | 2.571279 | 61 | <--Good! | | | |
| 28 | 13783 | 49.06186 | 4.225817 | 679 | 48.4412 | 4.855538 | 1403 | <--Fail | | | |
| 29 | 13784 | 50.14103 | 2.030251 | 156 | 50.87023 | 2.315157 | 131 | <--Good! | | | |
| 30 | 13785 | 48.47253 | 5.075868 | 182 | 50.50877 | 4.227549 | 228 | <--Good! | | | |

FIG.5

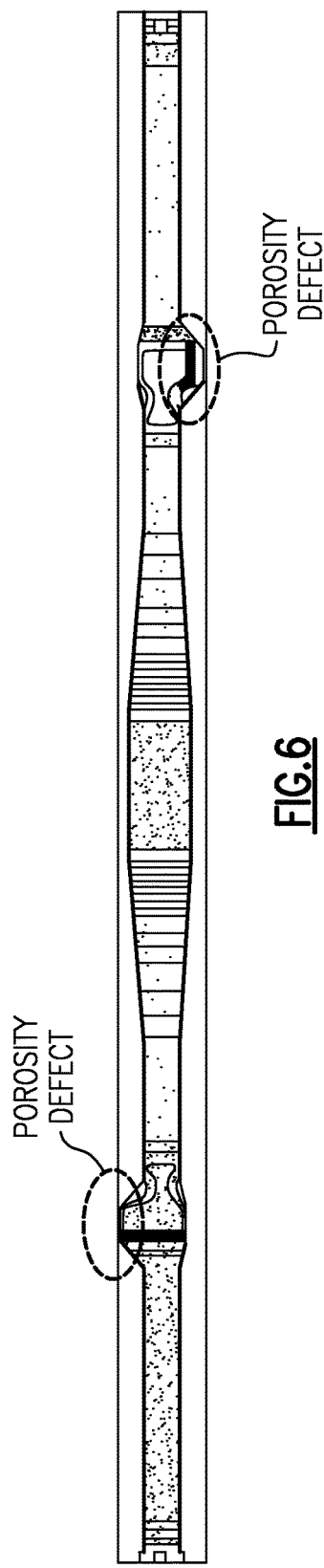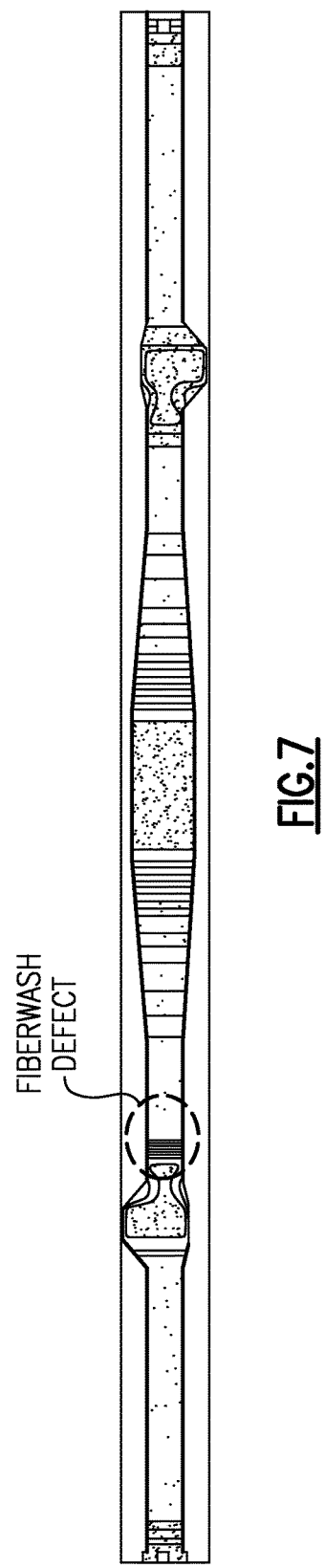

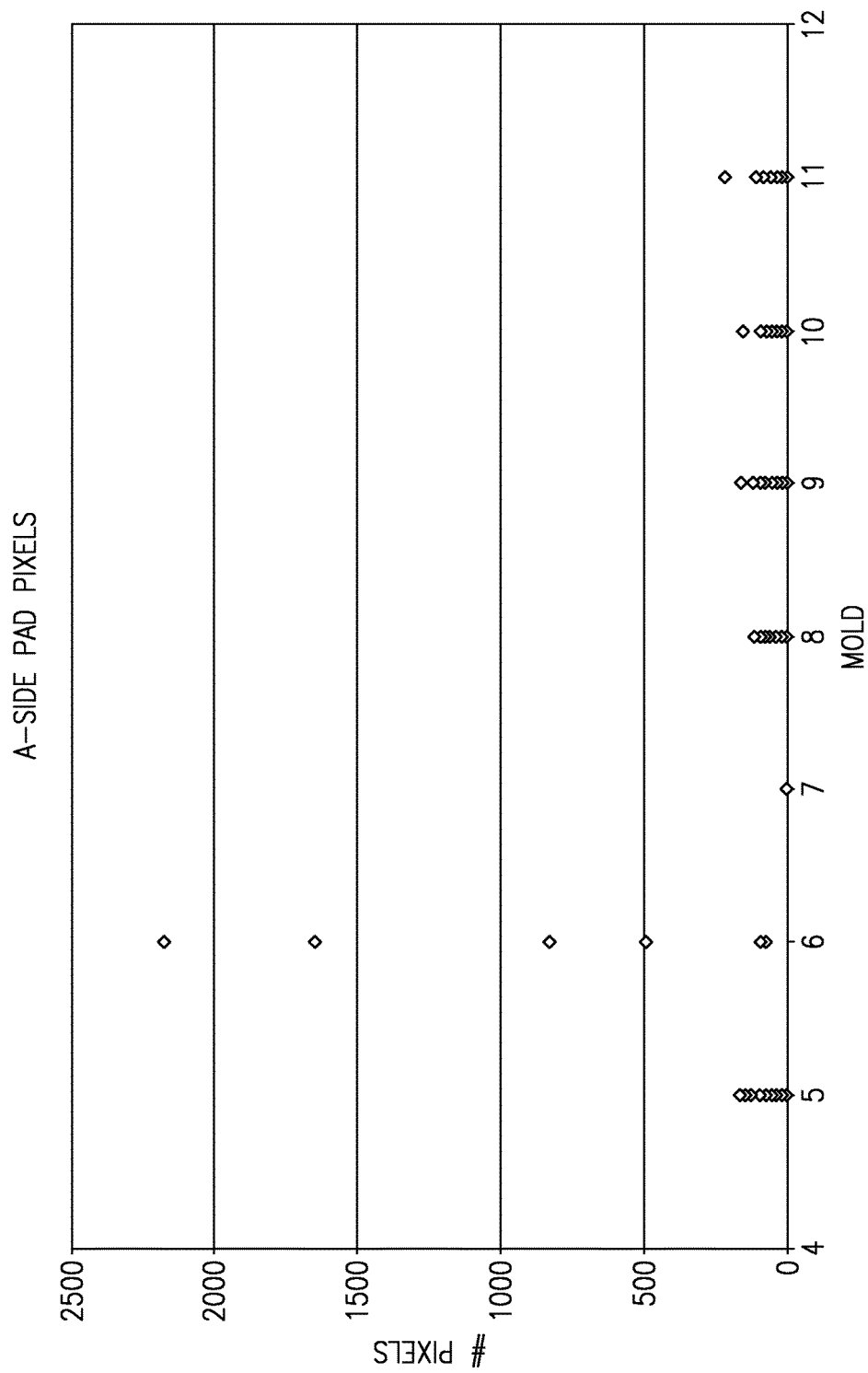

NON-DESTRUCTIVE INSPECTION METHOD WITH OBJECTIVE EVALUATION

BACKGROUND

The present application relates to a non-destructive inspection method, and more particularly to an automated process to objectively evaluate a test scan.

Ultrasonic Test (UT) scans are performed on various aerospace components such as composite tail rotor spars of a rotary-wing aircraft. When the UT scan is complete, a color-coded map is displayed and an inspector visually reviews the UT scan. The inspector subjectively decides the periphery of each defect based on comparison with a standard to determine whether predefined acceptance criteria have been achieved. The decision based on the predefined acceptance criteria results in a pass/fail indication.

The procedure may be time consuming and somewhat arbitrary as the result is at least partially subjective and dependant upon the inspector. Moreover, the variability may compromise the establishment of process improvement and quality trend data over the multitude of inspectors and the associated subjectivity.

SUMMARY

A method of non-destructive inspection evaluation according to an exemplary aspect of the present application includes: converting a scan file of at least a particular section of a part into a text file; evaluating the text file for a signal attenuation representative value within the particular section of the part; determining whether the signal attenuation representative value is greater than a predetermined value; and outputting a numeric score related to the signal attenuation representative value to signify a defect.

BRIEF DESCRIPTION OF THE DRAWINGS

Various features will become apparent to those skilled in the art from the following detailed description of the disclosed non-limiting embodiment. The drawings that accompany the detailed description can be briefly described as follows:

FIG. 3 is a plan view of a representative spar which is separated into sections for analysis through an ultrasonic test (UT) scan;

FIGS. 4A-4G illustrate different layers of an ultrasonic test (UT) scan which represent several "channels" of the UT scan;

FIG. 5 is a screen shot which illustrates a multitude of representative spars which are to be analyzed by the ScanScore software;

FIG. 6 is an example scan of a part that has porosity in both pad regions (at approximately ¼ and ¾ along the length of the part);

FIG. 7 is an example scan of a part that has fiberwash in the "wrist" region (at approximately ⅓ along the length of the part); and FIG. 8 is a chart which illustrates summary data of a representative spar with respect to the mold utilized in fabrication thereof.

DETAILED DESCRIPTION

Figure 1:
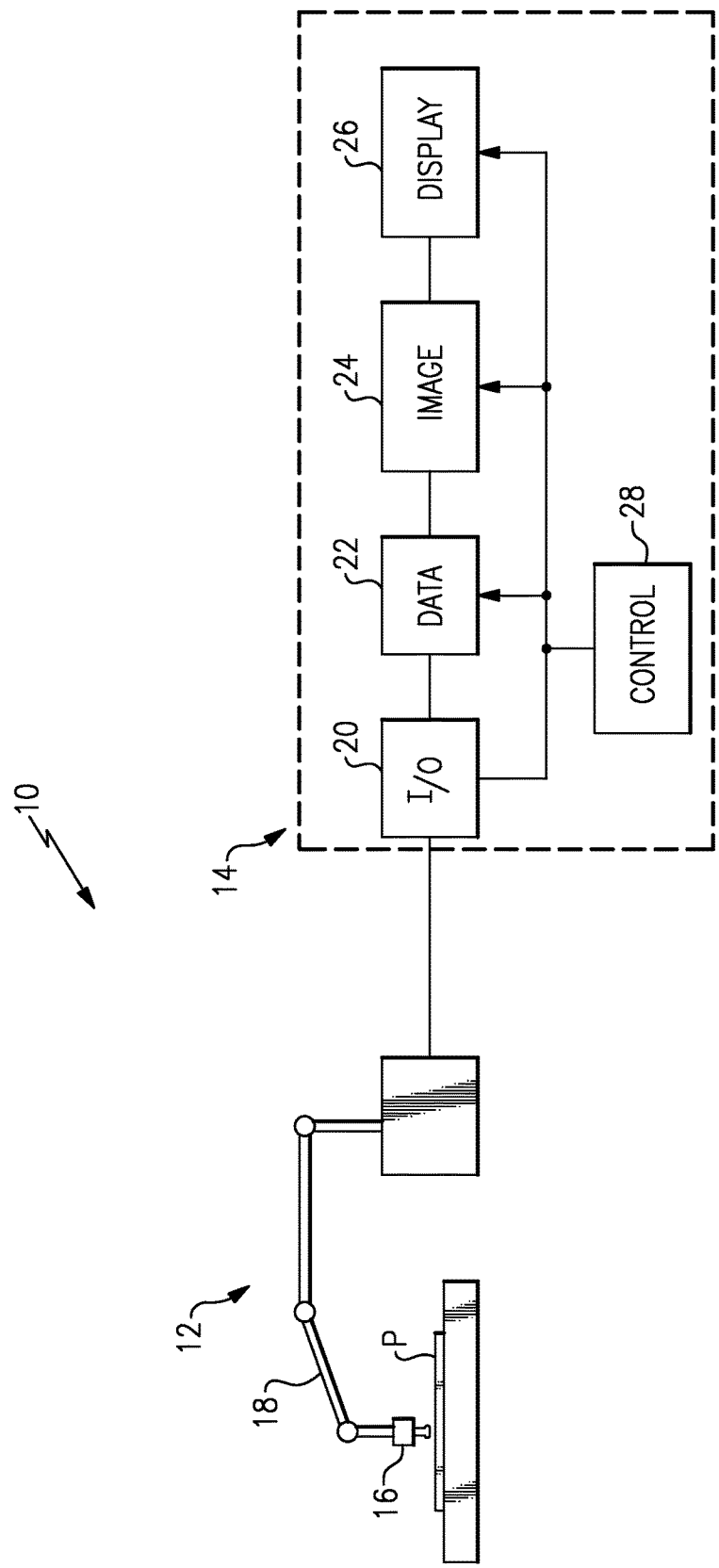
FIG. 1 is a schematic block diagram of a non-destructive inspection system.

FIG. 1 schematically illustrates a non-destructive inspection system 10. The non-destructive inspection system 10 generally includes an acquisition system 12 and a computer system 14 in communication therewith. The acquisition system 12 may provide an ultrasonic test (UT) scan, X-ray scan, or other map-based scan for objective evaluation through software within the computer system 14.

The software, referred to herein as ScanScore, gathers, processes, and analyzes the parts scanned by the non-destructive inspection system 10 to determine whether each part, or section thereof will "pass" or "fail" dependant on the colors and patterns in the scan relative to predetermined requirements.

The acquisition system 12 for a UT scan generally includes a probe 16 mounted to a mechanical arm 18 whose movement is precisely controlled by the computer system 14. The mechanical arm 18 is controlled to move the probe 16 over the surface of a part P. As the probe 16 moves across the part P, ultrasonic test data is taken at preprogrammed data points. While the data points are typically equally spaced, the computer system 14 may alternatively be programmed to take data at irregular distances. The acquisition system 12, in addition to one or more probes 16 may include interface electronics and an electromechanical apparatus to move the probe 16 across the surface of the part. The acquisition system 12 may also include position sensors that monitor the position of the probe 16.

The computer system 14 may include an interface 20, a data processor 22, an image processor 24, a display 26, and a control system 28. The interface 20 communicates with the probe 16 to communicate signals from the probe 16 to the data processor 22. The data processor 22 generates data in response to the signals provided from the interface 20. The data from the data processor 22 may be utilized such that the image processor 24 will output an image signal in response to the data produced by the data processor 22. The display 26 may be utilized with the control system 28 by a user to display image and other data from the data processor 22 and the image processor 24 as well as program and control the acquisition system 12.

The data processor 22 may include, for example, a processor and a memory device which, in response to a command issued from the control system 28, processes the signal from the interface 20 and generates data from the part P. For example, the data processor 22 performs a logarithmic amplification for the echo signal outputted from the probe 16, detects an envelope therefrom and generates data representative thereof. Numerical values may be assigned to the amount of signal attenuation for use in, for example, ASCII files.

The image processor 24 may include, for example, a processor and a memory device which, in response to a command issued from the control system 28, processes the signal from the interface 20 and generates an image on the display 26. The image processor 24 generates image data in predetermined channels and stores the generated image data into memory whereby a multi-dimensional dynamic image display or the like is effectuated. For example, colors may be mapped as representative of signal attenuation and utilized as the image data.

The display 26 includes, for example, a screen for the display of an ultrasonic image. The display 26 may be based on technologies such as cathode-ray tubes, liquid-crystal displays, organic light-emitting diodes, or other technologies.

The control system 28 is provided with, for example, a keyboard and a pointing device which, in accordance with an input operation, outputs a control signal. The control system 28 may be coupled to system interface and may include input devices, inclusive of but not limited to, a keyboard, mouse, scanner, microphone, camera, proximity device, etc. Further, the control system 28 may also include output devices, inclusive of but not limited to, a printer, storage, etc. Finally, the control system 28 may further include devices that communicate both as inputs and outputs, inclusive of but not limited to, a modulator/demodulator for accessing another device, system, or network, a radio frequency (RF) or other transceiver, a telephonic interface, a bridge, a router, etc.

The acquisition system 12, in one non-limiting embodiment, may be of the form of any non-destructive test equipment inclusive of, but not limited to, ultrasonic test equipment operable to provide an ultrasonic test (UT) scan of various materials for discontinuities. Such discontinuities may include flaws, a void or area of resin porosity, a delamination, foreign matter, or a change in stiffness caused by a composite ply formed of an unacceptable material, etc. As is well known to those skilled in the ultrasonic test art, different types of industrial ultrasound tests may be used to conduct, for example, through transmission ultrasound (TTU) and pulse echo (PE) ultrasound tests. In a TTU test, sound waves produced by an ultrasonic transmitter located on one side of the test part and received by a receiver located on the opposite side of the part pass completely through the test part. PE ultrasound test apparatus uses a single transducer located on one side of the test part that functions as both a transmitter and a receiver. Pulse echo testing requires access to only one side of the test part.

Figure 2:
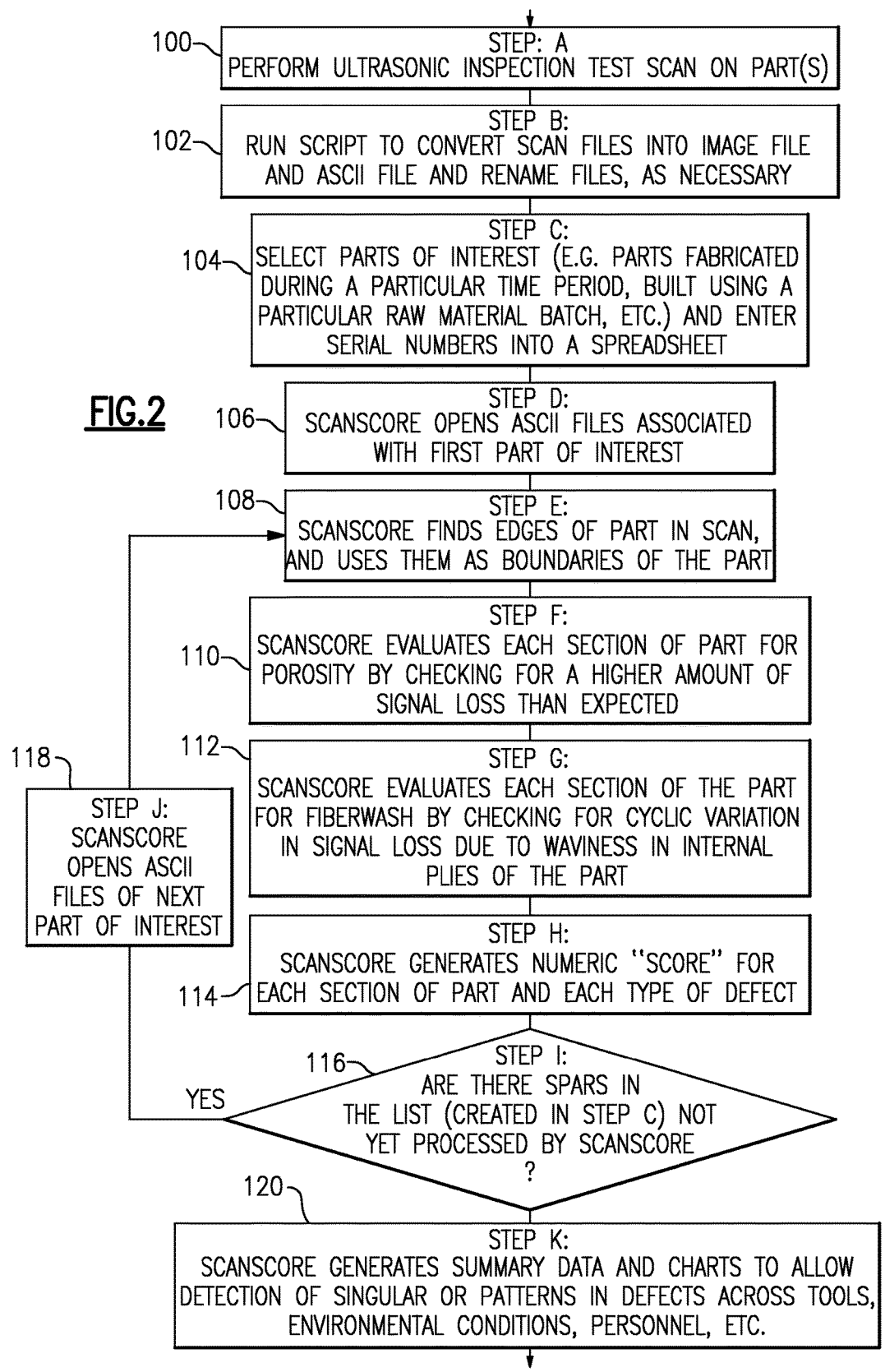
FIG. 2 is a flow chart which executes ScanScore software according to the present application with ultrasonic test (UT) scans obtained from an acquisition system.
Figure 4B:
Figure 4C:
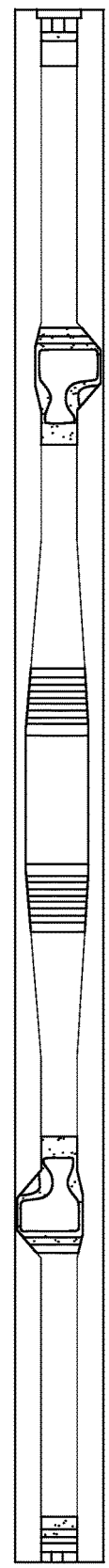
Figure 4D:
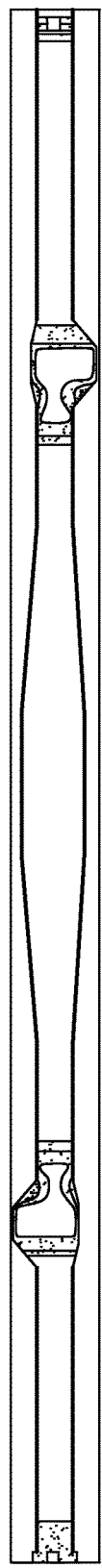
Figure 4E:
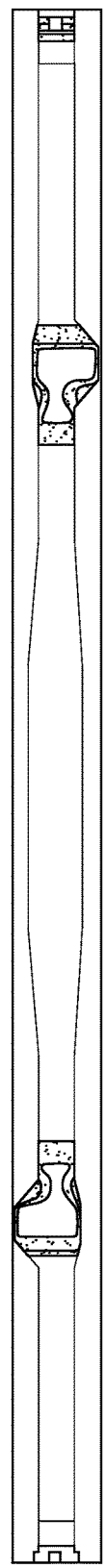
Figure 4F:
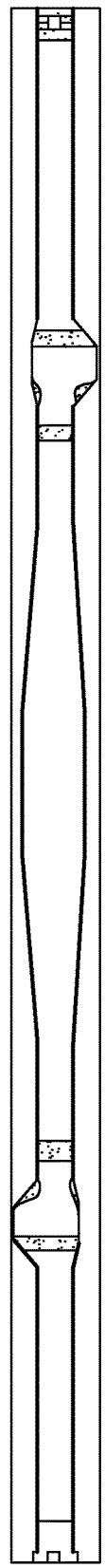
Figure 4G:
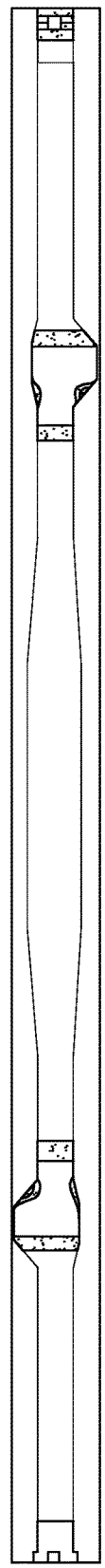

Referring to FIG. 2, the computer system 14 may be utilized to execute the ScanScore software with ultrasonic test (UT) scans obtained from the acquisition system 12. It should be understood that the computer system 14 may be in direct communication with the acquisition system 12 or may be remote therefrom such that the computer system 14 will store data such as scan files from the acquisition system 12 to be processed at a separate workstation. In FIG. 2, the operation of the ScanScore software is disclosed in terms of functional block diagrams.

Initially, an ultrasonic test (UT) scan is performed on each part (step 100). In this particular embodiment, the part is a tail rotor spar, however, various parts will also be usable herewith. The ultrasonic test (UT) scan is herein referred to as a scan file which may be associated with each part such as by serial number then stored in memory for later operations. It should be understood that the scan file may be obtained from various sources.

The scan files are converted into an image file (a representation of which is shown in FIG. 3) and a text file (Step 102). The scan files are the files output from the acquisition system 12. The image file may be a digital picture file for visual review and comparison. The text file may be an all text file such as an ASCII file. In one non-limiting embodiment, the text file is the file upon which the ScanScore software operates, although any other file type such as a binary file type may be used. The files are essentially equivalent in the information contain therein, but the image file is a visual reference of the text file so, for example, a section of the part would be represented by a grid of X points by Y points. Each point would have a numeric value which represents the signal attenuation at that given point. The numeric values are mapped as an image file in which the signal attenuation is represented by a color scale. The image file may contain multiple layers, each of which is representative of different "channels" provide by the UT scan. (FIGS. 4A-4G). Higher signal attenuation, for example, may be represented by black and progressively lower signal attenuation would proceed along a color scale. Particular colors may represent areas where signal attenuation is significant. That is, certain colors might be representative of voids or improperly oriented fibers.

Once all the scan files are converted into a respective image file and text file, particular parts of interest are selected (step 104). The parts may, for example, be selected in response to parts fabricated during a particular time period, fabricated based upon a particular raw material batch, etc.

The parts may be referenced through serial numbers as significant environmental information is typically tracked during manufacture and related to serial number. Furthermore, the scan file name might have an extension or other extraneous information. Through renaming of the file, each file may be identified by just the serial number such that each file is uniquely identified. The particular parts of interest may be input into a spreadsheet format in which the serial numbers are utilized to reference the parts (FIG. 5). For example only, tens of thousands of parts may have been scanned over a production run, but only the parts fabricated in a particular month may be selected.

The ScanScore software proceeds through the particular parts of interest selected in step 104 (Step 106). The ScanScore software first obtains the ASCII file associated with the first part of interest and opens that file.

The ScanScore software opens the particular ASCII file and determines the perimeter of the part (Step 108). That is, the UT scan is typically provided in X-Y coordinates over a rectangular pattern but the part itself will likely fall within the rectangular pattern. Without finding the perimeter for each part, there may be a risk of analyzing the wrong areas, not correctly relating the particular sections of the parts, or analyzing an area where there is no part at all. This may not be essential if each part is indexed to the same position on the acquisition system 12, but the perimeter identification assures any discrepancies are minimized or eliminated. The perimeter of the part is determined by finding the portion of the scan where there is a jump in signal attenuation, which is indicative of the start of a part. In the particular case of tail rotor spars, we take a jump of at least 50 units on a 0-255 scale of signal attenuation as the boundary of a part.

The perimeter of the part may be further defined into sections by the coordinates on the part. For example, the sections of the example spar are separated into right and left outboard sections, pad sections, wrist sections, torpedo sections and a center section (FIG. 3). Each section may defined by the design blueprint to have a permitted defect allocation.

The ScanScore software evaluates each section of the part for porosity by evaluating the text file for porosity defect (Step 110). That is, the text file is evaluated to determine a signal attenuation representative value which equates to any anomaly within the particular section. The anomaly is a determination of whether a value of the signal attenuation and the area of signal attenuation are greater than a predetermined value and area within each particular section of the part.

Signal attenuation also correlates to part thickness, among other characteristics such as density, surface roughness, etc. Because the part thickness varies in spars, there is a need to use a different number as the cutoff for signal attenuation that signifies a defect. ScanScore is calibrated to count the number of instances/pixels of signal below a threshold value, where the threshold value varies with the part thickness. The threshold value was chosen for each section of the part so that in one non-limiting embodiment, a value of 1000 "bad" pixels will display "FAIL" in the spreadsheet. Alternatively, the same threshold value can be used for all sections and the number of "bad" pixels required to "FAIL" a part can be varied. A particular section of a part may be discounted if there is a known factor that may cause signal attenuation. For example, near the center of each spar, there is a thermocouple installed. The thermocouple causes a discontinuity in part thickness, part density, and fiber orientation. These all cause different signal attenuation as compared to the surrounding area.

The predetermined value and area are typically defined by the design blueprint in which an anomaly such as a particular porosity defect is permitted within each section. The porosity defect is representative of voids which are represented by the signal attenuation. That is, if there is less signal in one area than another and the areas are of equivalent material and thickness, the signal attenuation would be indicative of a void, delamination or some other type of discontinuity referred to herein as a porosity defect (FIG. 6).

The ScanScore software then evaluates the text file for another predetermined anomaly such as a fiberwash defect (Step 112). The fiberwash defect is a determination of whether the signal attenuation is of a cyclic variation. That is, if the fiber reinforcements in the part are wavy or otherwise distorted, there is a periodic or cyclic signal attenuation (FIG. 7). One way to detect this type of defect is to identify and locate all of the areas where there is signal attenuation, then check for periodicity in the pattern of the defects. For example, the center of each defect may be located and the distance between them may be analyzed for patterns. The signal attenuation of each defect may be less than that required to be classified as a porosity defect, though it need not be less (i.e., pattern matters more than level of signal attenuation in this case). Typically, the cyclic variation or other pattern effect is readily identifiable by the ScanScore software. Furthermore, other patterns may be predefined for identification within each section of the part.

The ScanScore software then outputs a numeric score for porosity defect and fiberwash defect for each section of the part (Step 114). That is, an objective interpretation is provided for the amount of porosity defect and the amount of fiberwash defect which are translated into a numeric score for each section. Each part is associated with a series of numeric scores for each section of the part.

Alternatively, or in addition thereto, a multiple of scores may be combined into a single score. There are many methods that the scores can be combined. One method is to simply add the scores together, but this may assign lower than expected scores if there are many small but acceptable defects. Another way is to assign a simple "PASS" or "FAIL" to each section and have the final score reflect whether every section is acceptable, resulting in a "PASS" if all sections are acceptable and resulting in a "FAIL" if any one or more sections are not acceptable. This method gives an accurate account of whether a spar is acceptable, but does not provide as much information about the part. The scores can be weighted and averaged. For example, if a particular section of the part is of more interest than the rest for a particular analysis, but a general sense about that the remainder of the part is desired, more weight can be placed on the section of interest and less on the other sections. Scores may also be combined for multiple spars. If the performance of a particular batch of material is desired, for example, all the scores of the spars from that batch may be combined for a total score and compared to the total score of other batches of material.

Most parts have different criteria for different sections of the part. For the spar described herein, sections closer to the root ends generally experience higher loads such that a smaller allowable defect is permitted than the tip sections. Portions that are thinner generally experience a higher stress because even though the load is equivalent there is less cross-sectional area and a smaller allowable defect is permitted. Sections that are outboard or sections that are relatively thick generally experience a lower stress and have a larger allowable defect. Sections that are subjected to higher torsional stresses usually have a smaller allowable defect. It should be understood that various sections for various parts would have particular allowable defects which are defined by blueprint requirements translated into numeric scores. Furthermore, known sized defects in a template of flawed parts may be utilized to "calibrate" the measurements and allowable defects to determine the numeric scores. That is, predetermined porosity defects and fiberwash defects may be used to define a numeric score, and thereby relate a calculated numeric value for each measured part to an acceptable porosity defects and/or fiberwash defect so that the measured part may be identified as "passing" or "failing" inspection. The ScanScore software then loops through each additional part of interest selected in step 104 (Steps 116, 118). The ScanScore software thereby determines whether each part "passes" or "fails" based on the objective numeric criteria. Such determinations avoid the subjective evaluation typical of human inspection methods.

The ScanScore software may then be utilized to generate summary data to facilitate identification trends (Step 120). The ScanScore software generates summary data and charts to allow detection of singular or patterns in defects across, for example only, tools, environmental conditions, personnel, etc.

Referring to FIG. 8, the ScanScore software provides a summary output. An example conclusion may be that there is an issue with mold #6, which produces more pad porosity than the others. The chart identifies differences between molds, but the ScanScore software may alternatively be utilized to display, for example only, differences between material batches, days of the week, environmental conditions, etc. The chart of FIG. 8 is with reference to pad porosity, but other charts may be selected to plot fiberwash in the pad and other defects in other sections of the part in a summary type format.

It should be understood that relative positional terms such as "forward," "aft," "upper," "lower," "above," "below," and the like are with reference to the normal operational attitude of the vehicle and should not be considered otherwise limiting.

It should be understood that like reference numerals identify corresponding or similar elements throughout the several drawings. It should also be understood that although a particular component arrangement is disclosed in the illustrated embodiment, other arrangements will benefit herefrom.

Although particular step sequences are shown, described, and claimed, it should be understood that steps may be performed in any order, separated or combined unless otherwise indicated and will still benefit from the present invention.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be understood that within the scope of the appended claims, the invention may be practiced other than as specifically described. For that reason the appended claims should be studied to determine true scope and content.

What is claimed is:

1. A method of non-destructive inspection evaluation of a part comprising:
   converting a scan file of at least a particular section of a part into a text file;
   evaluating the text file for a signal attenuation representative value within the particular section of the part;
   determining whether the signal attenuation representative value is greater than a predetermined value; and
   outputting a numeric score related to the signal attenuation representative value to signify a defect.

2. A method as recited in claim 1, further comprising:
   associating the predetermined value with a porosity defect value;
   identifying that a porosity defect is associated with the particular section of the part in response to a determination that the signal attenuation representative value is greater than the predetermined value.

3. A method as recited in claim 2, further comprising:
   relating the predetermined value to a calibrated porosity defect value.

4. A method as recited in claim 2, further comprising:
   identifying the part as failed for porosity defect in response to a determination that the signal attenuation representative value is greater than a predetermined value.

5. A method as recited in claim 1, further comprising:
   associating the predetermined value with a cyclic variation; and
   identifying that a fiberwash defect is associated with the particular section of the part in response to a determination that the signal attenuation representative value is greater than the predetermined value.

6. A method as recited in claim 5, further comprising:
   relating the predetermined value to a calibrated fiberwash defect value.

7. A method as recited in claim 5, further comprising:
   identifying the part as a failed part for fiberwash defect in response to a determination that an area of the cyclic variation and signal attenuation in the area meet a predetermined criterion.

8. A method as recited in claim 1, further comprising:
   storing a numeric score for each of a multiple of parts, the numeric score including at least one signal attenuation representative value; and
   grouping the numeric scores for each of the multiple of parts by at least one parameter.

9. A method as recited in claim 8, further comprising:
   grouping the numeric scores for each of the multiple of parts by a mold number.

10. A method as recited in claim 8, further comprising:
    determining a trend from the numeric scores for each of the multiple of parts by the at least one parameter.

11. A method as recited in claim 8, further comprising:
    correlating the numeric score to a part characteristic.

12. A method as recited in claim 11, further comprising:
    relating the part characteristic to part thickness.

13. A method as recited in claim 11, further comprising:
    converting the scan file of the part into an image file of the part; and
    storing the image file of the part for display to a user.

14. A method as recited in claim 1, further comprising:
    performing an ultrasonic test on the part to generate the scan file.

15. A method as recited in claim 11, further comprising:
    associating the predetermined value with a cyclic variation; and
    identifying that a fiberwash defect is associated with the particular section of the part in response to a determination that the signal attenuation representative value is greater than the predetermined value.

16. A method as recited in claim 15, further comprising:
    relating the predetermined value to a calibrated fiberwash defect value.

17. A method as recited in claim 15, further comprising:
    identifying the part as a failed part for fiberwash defect in response to a determination that an area of the cyclic variation and signal attenuation in the area meet a predetermined criterion.

18. A method as recited in claim 1, wherein the converting comprises converting the scan file of a plurality of sections of the part into at least one text file, at least one of the sections defined by a design blueprint to have a permitted defect allocation different than another of the sections.

19. A method as recited in claim 1, wherein the part is a spar.

20. A method as recited in claim 1, wherein the part is a composite aircraft component.

21. A method as recited in claim 1, wherein the part has a contoured surface.

* * * * *